United States Patent
Fischer et al.

(10) Patent No.: US 12,428,298 B2
(45) Date of Patent: Sep. 30, 2025

(54) HYDROXYAPATITE POWDER AND METHOD FOR PRODUCING SAME

(71) Applicant: Chemische Fabrik Budenheim KG, Budenheim (DE)

(72) Inventors: Erhard Fischer, Ingelheim (DE); Stefan Mallmann, Heidesheim (DE); Christian Litterscheid, Ober-Olm (DE)

(73) Assignee: Chemische Fabrik Budenheim KG, Budenheim (DE)

( * ) Notice: Subject to any disclaimer, the term of this patent is extended or adjusted under 35 U.S.C. 154(b) by 418 days.

(21) Appl. No.: 17/601,856

(22) PCT Filed: Mar. 31, 2020

(86) PCT No.: PCT/EP2020/059070
§ 371 (c)(1),
(2) Date: Oct. 6, 2021

(87) PCT Pub. No.: WO2020/212131
PCT Pub. Date: Oct. 22, 2020

(65) Prior Publication Data
US 2022/0194797 A1 Jun. 23, 2022
US 2024/0182303 A2 Jun. 6, 2024

(30) Foreign Application Priority Data
Apr. 8, 2019 (DE) .................. 10 2019 109 143.8

(51) Int. Cl.
| | |
|---|---|
| C01B 25/32 | (2006.01) |
| A23L 29/00 | (2016.01) |
| A23L 33/16 | (2016.01) |
| A61G 11/00 | (2006.01) |
| A61K 8/24 | (2006.01) |
| A61Q 11/00 | (2006.01) |
| C04B 14/36 | (2006.01) |
| C08K 3/32 | (2006.01) |
| F16D 69/02 | (2006.01) |

(52) U.S. Cl.
CPC .......... *C01B 25/322* (2013.01); *A23L 29/015* (2016.08); *A23L 33/16* (2016.08); *A61K 8/24* (2013.01); *A61Q 11/00* (2013.01); *C04B 14/366* (2013.01); *C08K 3/32* (2013.01); *F16D 69/02* (2013.01); *A23V 2002/00* (2013.01); *A61K 2800/28* (2013.01); *C01P 2004/50* (2013.01); *C01P 2004/61* (2013.01); *C01P 2004/62* (2013.01); *C01P 2006/11* (2013.01); *C01P 2006/12* (2013.01); *C08K 2003/325* (2013.01); *C08K 2201/005* (2013.01); *C08K 2201/006* (2013.01); *F16D 2200/0034* (2013.01)

(58) Field of Classification Search
None
See application file for complete search history.

(56) References Cited

U.S. PATENT DOCUMENTS

| | | | |
|---|---|---|---|
| 5,180,564 A | 1/1993 | Wahl et al. | |
| 5,405,436 A * | 4/1995 | Maurer | A61K 8/24 424/602 |
| 7,998,219 B2 | 8/2011 | Riman et al. | |
| 8,974,848 B1 * | 3/2015 | Carothers | A61Q 11/00 424/1.73 |
| 2003/0118518 A1 | 6/2003 | Hahn et al. | |
| 2004/0171471 A1 | 9/2004 | Norenberg et al. | |
| 2008/0206554 A1 | 8/2008 | Riman et al. | |
| 2009/0130150 A1 * | 5/2009 | Gazzaniga | B82Y 5/00 424/641 |
| 2010/0303702 A1 | 12/2010 | Ogawara | |
| 2013/0260341 A1 * | 10/2013 | Sibbett | A61B 5/0088 106/35 |

FOREIGN PATENT DOCUMENTS

| | | |
|---|---|---|
| AU | 2004256947 B2 | 1/2009 |
| DE | 11 2011 101 920 T5 | 5/2013 |
| DE | 10 2014 115 518 A1 | 4/2016 |
| EP | 0 486 813 A1 | 5/1992 |
| EP | 1 044 671 A2 | 10/2000 |
| EP | 1139995 A1 | 10/2001 |
| EP | 1 401 762 | 3/2004 |
| JP | H01234308 A | 9/1989 |
| WO | WO-98/18719 A1 | 5/1998 |
| WO | WO-00/37033 A1 | 6/2000 |
| WO | WO-2012/009555 A2 | 1/2012 |

OTHER PUBLICATIONS

English translation of Kobayashi et al. (JP 2014-059306). (Year: 2014).*
English translation of Itoi et al. CN-1239929 (Year: 1999).*
Toriyama, M. et al., "Synthesis of Hydroxyapatite by an Oxidative Decomposition Method of Calcium Chelate," Journal of the Ceramic Society of Japan, International Edition, Fuji Technology Press, Tokyo, JP, vol. 100, No. 7, Jul. 1, 1992, pp. 939-943.
DWPI-Abstract/-Data for JP H02-180706 A.
Kumar, R., et al., "Temperature Driven Morphological Changes of Chemically Precipitated Hydroxyapatite Nanoparticles," Langmuir 2004, vol. 20, pp. 5196-5200.

* cited by examiner

*Primary Examiner* — Ronak C Patel
(74) *Attorney, Agent, or Firm* — MEDLER FERRO WOODHOUSE & MILLS PLLC

(57) ABSTRACT

In order to provide a hydroxyapatite that can be used without reservation in the food industry, a hydroxyapatite powder is provided composed of primary particles. The median size of the primary particles from which the powder is made is >0.10 μm and the aspect ratio of the primary particles is <5. The specific surface area of the hydroxyapatite powder is ≤10 m²/g, and the bulk density is >550 g/l. Also disclosed is a method with which such a hydroxyapatite powder can be obtained.

12 Claims, No Drawings

HYDROXYAPATITE POWDER AND METHOD FOR PRODUCING SAME

CROSS REFERENCE TO RELATED APPLICATIONS

This application is a National Stage of International Application No. PCT/EP2020/059070 filed Mar. 31, 2020, which claims benefit of German Patent Application No. 10 2019 109 143.8 filed Apr. 8, 2019, both of which are herein incorporated by reference in their entirety.

The present invention relates to a hydroxyapatite powder consisting of particles having special properties that relate in particular to the particle size. The present invention further relates to a method for producing such a hydroxyapatite powder in which milk of lime is reacted with phosphoric acid to form hydroxyapatite. The present invention also relates to the use of the hydroxyapatite powder according to the invention in a variety of fields of application.

Hydroxyapatite forms in aqueous systems at temperatures up to 100° C. as primary particles in which at least one spatial axis is <0.10 µm in dimension. At higher temperatures (>100° C.), e.g. by hydrothermal synthesis (150-250° C.) or flux synthesis (400-700° C.), it is possible to obtain primary particles that have edge lengths >0.10 µm in all spatial directions. However, these primary crystals have a columnar shape and result in a powder with a relatively large specific surface area in the range around 70 m$^2$/g. The bulk densities of these materials are typically in the range of 200-350 g/l.

On a large scale, hydroxyapatite is usually produced by reacting milk of lime with phosphoric acid, which creates very fine, acicular primary particles that can agglomerate to form secondary particles in the micrometer range. Methods are sometimes also described, in which precipitation is carried out in an autoclave under elevated pressure at temperatures above 100° C. (e.g., EP 1 401 762). Hydroxyapatite can alternatively also be obtained by precipitating aqueous solutions of water-soluble calcium salts in the presence of water-soluble phosphate or fluoride salts. In some cases, this involves the addition of water-soluble surfactants, water-soluble polymeric protective colloids or chelating agents, such as EDTA (see EP 1 139 995 and U.S. Pat. No. 7,998,219 B2).

Due to the structure and size of the primary particles of the hydroxyapatite materials obtained with the aforementioned method, such products fall under the definition of the term "nanomaterial" as defined by the Commission of the European Union on Oct. 18, 2011 (2011/696/EU). According to this definition, a "nanomaterial" is a material that contains particles in an unbound state, as an aggregate or as an agglomerate, and in which at least 50% of the particles in the number size distribution have one or more external dimensions in the range of 1-100 nm.

Since "nanomaterials" are recently being viewed more and more critically, especially in food technology, due to their ability to penetrate biomembranes, there is a need, in particular for hydroxyapatite powders to be used in the food industry, for materials that are not nanomaterials as defined above. There is in particular a need for a method that can be used to selectively and reliably obtain a hydroxyapatite powder that does not exhibit any nano-properties.

One way in which such materials could theoretically be obtained is by sintering conventional hydroxyapatite powders together at temperatures in the range of 300-900° C. However, materials obtained in this way have very large specific surface areas, sometimes well in excess of 10.0 m$^2$/g, which is disadvantageous for applications in which the absorption properties associated with a large specific surface area are undesirable.

Another approach could be to influence the kinetics of formation of hydroxyapatite powders by varying the temperature during precipitation. In their publication "Temperature Driven Morphological Changes of Chemically Precipitated Hydroxyapatite Nanoparticles" (Langmuir 2004, 20, 5196-5200), Kumar, R., et al. describe the effect of temperature on the morphology of precipitated hydroxyapatite particles. This publication finds in particular that, at a temperature of approximately 40° C., acicular particles are obtained. At 80° C. the morphology of the obtained particles changes to a more pyramidal shape with a lower aspect ratio, and at 100° C. and above the particle morphology becomes spherical. In all three cases, however, the particle size is well within the nanometer range at least in one dimension. The smallest dimension of the needles obtained at 40° C., for example, is 25 nm and the particle diameter of the spherical particles obtained at 100° C. and above is 50 nm. Therefore all of these hydroxyapatite products fall under the above definition of "nanomaterials."

With this in mind, the object of the present invention is to provide a hydroxyapatite powder that does not fall under the above definition of "nanomaterials" and can therefore also be used in the food industry without the reservations associated with the use of nanomaterials.

The object of the present invention is achieved by providing a hydroxyapatite powder composed of primary particles, wherein the median of the primary particles from which the powder is made is >0.10 µm and the aspect ratio of the primary particles is <5, wherein the specific surface area of the hydroxyapatite powder is ≤10 m$^2$/g, and the bulk density is >550 g/l.

As already mentioned at the beginning, hydroxyapatite powders are typically composed of primary particles, which can in turn agglomerate to form secondary particles. The present invention is therefore characterized in that the primary particles of the hydroxyapatite powder have an aspect ratio of <5, whereby the aspect ratio is the ratio of the largest average dimension of the particles in a first dimension to the smallest average dimension of the particles in a second dimension.

As a result of the aspect ratio of <5 achieved according to the invention, the primary particles have a significantly higher compactness than is the case for acicular hydroxyapatite primary particles from the state of the art. The primary particles of the hydroxyapatite powder according to the invention preferably have an aspect ratio of <3 or even <2 and thus have a particularly high compactness. In these ranges, the primary particles have a cuboid or ovoid to almost spherical shape.

The aspect ratio is determined by means of optical analysis. For a portion of the powder, the largest dimension of the particles in a first dimension and the smallest dimension of the particles in a second dimension are measured under the scanning electron microscope and the statistical mean (arithmetic mean) of the respective values are related to one another.

The median of the primary particles of the hydroxyapatite powder according to the invention is above 0.10 µm and is determined using dynamic light scattering and based on the number of particles. In preferred embodiments of the invention, the median of the primary particles is >0.11 µm, more preferably >0.12 µm, particularly preferably >0.13 µm. The further away the median of the primary particles is from the limit value below which a nanomaterial is present according to the above definition, the lower the proportion of particles in this material that are below this limit, which is advantageous in particular for foodstuff applications in terms of the membrane permeability of such small particles mentioned at the beginning.

The upper limit of the median of the primary particles is preferably <10 µm, <9 µm, <8 µm, <7 µm, <6 µm or even <5 µm.

The specific surface area of the hydroxyapatite powder according to the invention is ≤10 m²/g and is determined by BET measurement using the absorption of nitrogen according to DIN ISO 9277. In preferred embodiments of the invention, the specific surface area of the hydroxyapatite powder is ≤8 m²/g and, in particularly preferred embodiments, ≤7 m²/g. As already mentioned at the beginning, for certain applications of the hydroxyapatite powder according to the invention, the smallest possible specific surface area is desirable and advantageous. From this point of view, depending on the specific requirements placed on the material, it is desirable to have hydroxyapatite powders available that have a particularly low specific surface area.

According to the invention, the bulk density of the hydroxyapatite powder is more than 550 g/l, and the bulk density is determined according to the method defined in DIN ISO 697 without compaction in a bulk density cylinder. Depending on the requirements, in certain embodiments, the present invention also achieves bulk densities of >600 g/l or even >650 g/l. This is advantageous in particular when the hydroxyapatite powder according to the invention is used as a free flowing agent in a mixture with powder materials having a correspondingly high bulk weight to improve the free flowing properties. The closer the bulk weight of the free flowing agent is to the bulk weight of the powder material to be mixed with it, the less the respective product is prone to separate. Examples of this are, for example, ceramic mixtures or mixtures of different metal salts for mineral enrichment.

According to the present invention, the term hydroxyapatite powder includes powdery materials that consist of at least 95 wt % $Ca_5(PO_4)_3OH$. The term therefore not only includes powders the particles of which consist of 100 wt % pure hydroxyapatite, but also powders that, for example, comprise a proportion of mixed crystals of hydroxyapatite with, for example, dolomite, as long as the total proportion of $Ca_5(PO_4)_3OH$ constitutes at least 95 wt % of the powder.

Depending on the specific conditions under which the hydroxyapatite powder according to the invention was produced (e.g., pH ≤7), it can also include small amounts of calcium hydrogen phosphate ($CaHPO_4$) or calcium hydrogenphosphate dihydrate ($CaHPO_4*2\ H_2O$) as a secondary phase, as long as the total proportion of $Ca_5(PO_4)_3OH$ is at least 90 wt % of the powder. This is in accordance with established FCC (Food Chemicals Codex) and pharmaceutical guidelines, which require a purity of at least 90% for a material to be designated as hydroxyapatite.

Preferred hydroxyapatite powders according to the present invention consist of at least 95 wt %, at least 97 wt %, at least 98 wt % or at least 99 wt % $Ca_5(PO_4)_3OH$.

The present invention also includes hydroxyapatite powders in which a proportion of up to 10 atomic percent of the calcium ions in the hydroxyapatite are replaced by foreign ions, such as magnesium, iron and zinc ions. In preferred hydroxyapatite powders according to the present invention, the proportion of calcium ions replaced by foreign ions is at most 5 atomic percent, at most 3 atomic percent, or only at most 1 atomic percent.

In certain embodiments of the invention, the hydroxyapatite that forms the powder is calcium-saturated hydroxyapatite with the stoichiometric formula $Ca_5(PO_4)_3OH$.

In other embodiments, the hydroxyapatite is calcium-deficient hydroxyapatite with the formula $Ca_{10-x}(PO_4)_{6-x}(HPO_4)_x(OH)_{2-x}$, where $0<x\leq2$. The saturation of hydroxyapatite is determined by means of X-ray fluorescence analysis (e.g., Malvern Panalytical, Axios, WDXRF). If the measured saturation is <3.33, it is a calcium-deficient hydroxyapatite. At 3.33 or above, it is a calcium-saturated hydroxyapatite.

At least 90 wt %, preferably at least 95 wt %, more preferably at least 98 wt %, of the primary particles of the hydroxyapatite powder according to the invention are agglomerated to form secondary particles. The median size of the secondary particles is >1.0 µm. In certain embodiments, the median of the secondary particles is >10.0 µm or even >100 µm.

In certain embodiments, the upper limit of the median of the secondary particles is <50 µm, <40 µm, <30 µm, <20 µm, <15 µm, <10 µm, <9 µm, <8 µm, <7 µm, <6 µm or even <5 µm.

The hydroxyapatite powder according to the invention can be obtained using a method in which a reaction mixture is created in which milk of lime is reacted with phosphoric acid to form hydroxyapatite, whereby this method is in particular characterized in that a method cycle comprising the following method steps is carried out:

a) providing a suspension of hydroxyapatite starter particles in water,
b) adding milk of lime and phosphoric acid to the suspension,
c) reacting the milk of lime with the phosphoric acid in the suspension to form hydroxyapatite
   at a temperature in the range of >20° C. and <105° C. and
   at a pH in the range from 6.0 to 13.0,
d) separating at least a portion of the hydroxyapatite particles out of the suspension,
e) repeating method steps a) to d) at least once, wherein either the hydroxyapatite particles separated in method step d) or the hydroxyapatite particles remaining in the suspension in method step d) are used as the hydroxyapatite starter particles in method step a), and
f) removing the hydroxyapatite particles which, in the dried state, have a median of the primary particles of >0.1 µm from the method cycle.

The advantages claimed for the present invention are already achieved if method steps a) to d) are repeated only once. However, even better results can be achieved if said method steps are repeated at least three times.

In one embodiment of the invention, the method is carried out in semicontinuous operation, wherein the portion of the hydroxyapatite particles separated in method step d), which, in the dried state, has a median of the primary particles of >0.10 µm, is always removed from the process, while the remaining portion is resuspended in water in method step a) to provide a suspension of hydroxyapatite starter particles in water.

In an alternative embodiment of the invention, the method is carried out in fully continuous operation, wherein, in method step d), the portion of hydroxyapatite particles which, in the dried state, has a median of the primary particles of >0.10 µm is continuously separated and removed from the method cycle while the remaining portion remains in the method cycle. The continuous separation and removal is preferably carried out using an inclined plate clarifier or a centrifuge (e.g.: inverting centrifuge or pusher centrifuge).

In a certain embodiment, hydroxyapatite starter particles with a median of <0.1 μm are used in method step a) and method steps a) to e) are repeated at least once to obtain a hydroxyapatite powder the primary particles of which have a median of >0.10 μm and an aspect ratio of <5, wherein the specific surface area of the hydroxyapatite powder is ≤10 $m^2/g$ and the bulk density is >550 g/l.

In a particular embodiment of the invention, the method is carried out in continuous operation, wherein a proportion of the hydroxyapatite particles separated in method step d), the primary particles of which have a median of >0.10 μm and an aspect ratio of <5 and the specific surface area of which is ≤10 $m^2/g$ and the bulk density of which is >550 g/l, is removed from the process, while the remaining portion is resuspended in water in method step a) to then undergo the repeated method steps b) to e).

The reaction of the milk of lime with the phosphoric acid should be as uniform and controlled as possible. For the success of the present invention, it is therefore crucial that the temperature in the reaction mixture is above 20° C. and below 105° C. In certain embodiments of the invention, the reaction of the milk of lime with the phosphoric acid in the reaction mixture to form hydroxyapatite takes place at a temperature in the range of >60° C. and <100° C. or at a temperature in the range of >80° C. and <100° C.

It is also critical to the success of the present invention that the pH be in the range of 6.0-13.0. At a pH of <6.0, calcium hydrogen phosphate ($CaHPO_4$) or calcium hydrogenphosphate dihydrate ($CaHPO_4*2\ H_2O$) precipitates. In certain embodiments of the invention, the reaction of the milk of lime with the phosphoric acid in the reaction mixture to form hydroxyapatite takes place at a pH in the range of 7.0 to 11.0, because under certain conditions $Ca(OH)_2$ can increasingly occur as a secondary phase at a pH above 11.0. In an alternative embodiment of the invention, the reaction to hydroxyapatite takes place at a pH in the range from 7.0 to 9.0, because under certain conditions at least some inclusions of $Ca(OH)_2$ can occur at a pH above 9.0.

In a certain embodiment of the invention, the reaction of phosphoric acid and milk of lime in the reaction mixture (method step c)) is carried out at atmospheric pressure. If desired, however, the method can also be carried out at slightly elevated pressure, preferably up to an overpressure of 1 bar.

In the final processing step, the particles obtained using the method according to the invention are washed with water, separated by filtration or centrifugation and dried. How specifically this is to be carried out is known to the skilled person and therefore requires no further explanation.

One of the educts of the method according to the invention is phosphoric acid ($H_3PO_4$). In certain embodiments, the phosphoric acid used is diluted phosphoric acid with a concentration of 5 to 25 vol % phosphoric acid in water. Low phosphoric acid concentrations facilitate the growth of germs, but also result in larger volumes of the reaction mixture. In certain embodiments, the concentration of phosphoric acid used is therefore in the range of 10 to 25 vol % phosphoric acid in water or in the range of 15 to 25 vol % phosphoric acid in water.

The second educt of the method according to the invention is milk of lime (suspension of $Ca(OH)_2$ in water). In certain embodiments of the invention, the oxide-based milk of lime has a concentration of 2 to 20 wt %, preferably 8 to 12 wt %.

According to the present invention, the milk of lime and the phosphoric acid can be added one after the other in method step b), whereby the time interval between the addition of these two educts should be as short as possible. Preferably, however, the milk of lime and the phosphoric acid are added to the batch at the same time.

According to the method according to the invention, the reaction of milk of lime with phosphoric acid is carried out in the presence of hydroxyapatite starter particles, the particle size of which is characterized by a median of <0.1 μm. In certain embodiments, these particles have a bulk density in the range of 200 to 350 g/l and a specific surface area in the range of 15 to 50 $m^2/g$.

In the method according to the invention, primary particles of the desired size and shape are obtained by repeated layering of hydroxyapatite layers during method step c). This is achieved by reacting the milk of lime added to the reaction mixture with the phosphoric acid added to the reaction mixture in situ to form hydroxyapatite.

For both the first time and for each repeated step, the repeated reaction of respectively freshly added milk of lime and freshly added phosphoric acid takes place in method step c) under stirring. The mechanical stress during stirring should be kept as low as possible. Consequently, in certain embodiments of the method according to the invention, the maximum speed of the outermost section of the stirrer in the plane of rotation is <2 m/s, more preferably <1 m/s and particularly preferably <0.5 m/s. If the mechanical stress on the reaction mixture is too high, new crystallization nuclei will form, which would hinder the process according to the invention of layering further hydroxyapatite layers onto already existing particles.

For both the first time and for each repeated step, the repeated reaction of respectively freshly added milk of lime and freshly added phosphoric acid preferably takes place in method step c) over a specific period of time.

The hydroxyapatite powder provided using the present invention can be put to a variety of uses. In one embodiment of the invention, the hydroxyapatite powder according to the invention is used to fortify foodstuffs, such as milk or cheese, with calcium. In a further embodiment, the hydroxyapatite powder according to the invention is used as a free flowing agent in foodstuffs to improve the flow properties thereof. Combined use, i.e., as both a free flowing agent and for calcium fortification, is possible as well.

In another embodiment, the hydroxyapatite powder according to the invention is used as a filler for plastics and ceramics or as an abrasive in toothpaste or as a hard material in brake linings.

EXAMPLES

Examples 1.1-1.4 describe different production methods for hydroxyapatite powder (HAP).

The analysis results of the thus produced materials are shown below in tables.

1.1 Conventional Method

An aqueous suspension of $Ca(OH)_2$ (calculated content of 10% CaO) is heated to 80° C. in a boiler. Then the appropriate quantity of 20% $H_3PO_4$ is added slowly until a pH of 7 is reached. The suspension is stirred for another 15 min. Then filtered off, washed and dried.

1.2 Method According to the Invention (Precipitation on Hydroxyapatite)

An aqueous suspension of HAP (material from 1.1) with a solids content of 13% is heated to 90° C. in a boiler; the batch quantity of HAP is 10% of the desired target quantity. Milk of lime with a calculated content of 10% CaO and 20% phosphoric acid are then added at the same time while maintaining a specific pH in the range of 7.0 to 9.0. The suspension is stirred for another 15 min. 90% of the suspension is then filtered off, washed and dried. The experiments for simultaneous precipitation were repeated seven more times (V2-V8) after the first precipitation (V1), in each case the remaining 10% served as the batch for the next precipitation according to said method.

1.3. Comparison Method (Precipitation on Ca(OH)$_2$)

100 mL milk of lime is provided in a 2 L reactor and measured with a pH electrode. The milk of lime (content: 10% CaO) is then added at 20 rpm via a peristaltic pump. Phosphoric acid (20%) is added at the same time via a process control system, such that a specific pH is present during precipitation. After reaching the >1 l filling mark, 400 ml of the preparation was removed and the remainder (in the PCS) was set to a pH of 7 with phosphoric acid. The tests were carried out with precipitation pH values of 10, 9, 8, 7 (V1-V8).

1.4 Comparison Method (Sintering Process)

Material from 1.1 is sintered together using a thermal treatment. To do this, the material was heated in Alusint crucibles to 300, 500 and 900° C. for 12 h respectively (V1-V3).

Analysis Methods and Results

The materials produced according to Examples 1.1-1.4 were analyzed using the following methods:

X-ray diffraction (XRD, Bruker D8 Advance, CuKα, 40 kV; 40.0 mA; A 1.5406 Å; Lynxeye detector), particle size distributions (PSD) by means of dynamic light scattering ("Horiba") based on both volume and particle size, specific surface area according to the BET method using $N_2$ absorption (DIN ISO 9277), shape and size using scanning electron microscope images (SEM).

1. Physical Specifications

A compilation of the experimentally determined analysis values for the materials produced according to the examples is provided in the following Tables 1 and 2.

TABLE 1

Overview of the analysis values from Experiments 1.1-1.2.

| Test no. | XRD | BET m$^2$/g | Bulk density g/l | Saturation (determined experimentally) | D10 Median D90 (Volume-based) | D10 Median D90 (Number-based |
|---|---|---|---|---|---|---|
| 1.1 | HAP | 65.8 | not determined | not determined | not determined | not determined |
| 1.2 (V0) | HAP | 16.7 | 260 | 3.33 | not determined | not determined |
| 1.2 (V1) | HAP | 14.7 | 530 | 3.23 | 15.29684(μm) 4.90018(μm) 0.68476(μm) | 0.24896(μm) 0.13929(μm) 0.09582(μm) |
| 1.2 (V2) | HAP | 10.0 | 570 | 3.27 | 11.70868(μm) 5.42478(μm) 0.32242(μm) | 0.22861(μm) 0.13090(μm) 0.08679(μm) |
| 1.2 (V3) | HAP | 8.0 | 620 | 3.27 | 11.56829(μm) 5.89078(μm) 0.32429(μm) | 0.22601(μm) 0.13107(μm) 0.08693(μm) |
| 1.2 (V4) | HAP | 7.4 | 630 | 3.28 | 11.92629(μm) 6.19286(μm) 0.35308(μm) | 0.23763(μm) 0.13482(μm) 0.08784(μm) |
| 1.2 (V5) | HAP | 7.4 | 640 | 3.27 | 11.94827(μm) 6.25612(μm) 0.35594(μm) | 0.23467(μm) 0.13396(μm) 0.08767(μm) |
| 1.2 (V6) | HAP | 6.5 | 660 | 3.27 | 11.94827(μm) 6.25612(μm) 0.35594(μm) | 0.23523(μm) 0.13436(μm) 0.08780(μm) |
| 1.2 (V7) | HAP | 6.0 | 670 | 3.27 | 10.95516(μm) 6.09562(μm) 0.43992(μm) | 0.22858(μm) 0.13270(μm) 0.08754(μm) |
| 1.2 (V8) | HAP | 6.2 | 650 | 3.26 | 11.19130(μm) 6.09160(μm) 0.36278(μm) | 0.22947(μm) 0.13279(μm) 0.08750(μm) |

TABLE 2

Overview of the analysis values from Experiments 1.3-1.4

| Test no. | XRD | BET m$^2$/g | Bulk density g/l | Saturation determined experimentally | D10 Median D90 (Volume-based) | D10 Median D90 (Number-based |
|---|---|---|---|---|---|---|
| 1.3 (V1) pH | HAP 10 | 102.1 | not determined | 3.07 | not determined | not determined |
| 1.3 (V2) pH | HAP 10 | 104.1 | not determined | 2.94 | not determined | not determined |
| 1.3 (V3) pH | HAP 9 | 89.5 | not determined | 3.04 | not determined | not determined |

TABLE 2-continued

Overview of the analysis values from Experiments 1.3-1.4

| Test no. | XRD | BET m²/g | Bulk density g/l | Saturation determined experimentally | D10 Median D90 (Volume-based) | D10 Median D90 (Number-based) |
|---|---|---|---|---|---|---|
| 1.3 (V4) pH | HAP 9 | 103.9 | not determined | 2.98 | not determined | not determined |
| 1.3 (V5) pH | HAP 8 | 80.6 | not determined | 3.04 | not determined | not determined |
| 1.3 (V6) pH | HAP 8 | 66.6 | not determined | 2.96 | not determined | not determined |
| 1.3 (V7) pH | HAP 7 | 75.9 | not determined | 3.01 | not determined | not determined |
| 1.3 (V8) pH | DCP-D 5 | 15.7 | 410 | 2.11 | not determined | not determined |
| 1.4 Un-treated* | | 75.5 | | | 7.46947 (µm) 4.03874 (µm) 2.01859 (µm) | 3.51947 (µm) 1.81696 (µm) 1.08566 (µm) |
| 1.4 (V1) 300° C. | HAP | 70.3 | not determined | not determined | not determined | not determined |
| 1.4 (V2) 500° C. | HAP | 49.6 | not determined | not determined | not determined | not determined |
| 1.4 (V3) 900° C. | HAP | 10.9 | not determined | not determined | not determined | not determined |

*granulated product

2. Investigation of Free Flow Properties

Hydroxyapatite powder produced according to the invention was used as free flowing agent for two different coffee whiteners (VB 30A and VG 80C) and compared with other free flowing agents (B-TCP=beta-tricalcium phosphate; E551=nano-SiO$_2$).

The maximum achievable angle of slope of the heaped material was determined and the results are summarized below in Table 3.

An angle of 31-40° represents good flow properties, an angle of 41 to 45° represents acceptable flow properties, and an angle of 46-55° represents poor flow properties.

TABLE 3

Overview of angles of repose of the free flow tests

| Test no. | Test substance | Proportion of free flowing agent [wt %] | Free flowing agent | Angle of slope [°] |
|---|---|---|---|---|
| 1 | VB 30A | 0.0 | — | 54.1 |
| 2 | VB 30A | 1.0 | B-TCP (C73-13) | 49.2 |
| 19 | VB 30A | 1.0 | 1.2 V8 | 44.4 |
| 20 | VB 30A | 2.0 | 1.2 V8 | 44.4 |
| 17 | VB 30A | 1.0 | 1.4 V3 | 38.7 |
| 18 | VB 30A | 2.0 | 1.4 V3 | 35.8 |
| 6 | VB 30A | 0.3 | E551, nano-SiO$_2$ | 31.8 |
| 7 | VG 80C | 0.0 | — | no information |
| 15 | VG 80C | 2.0 | B-TCP (C73-13) | 51.6 |
| 21 | VG 80C | 1.0 | 1.4 V3 | 49.7 |
| 11 | VG 80C | 0.5 | E551, nano-SiO$_2$ | 48.7 |
| 9 | VG 80C | 1.0 | 1.2 V8 | 46.7 |
| 22 | VG 80C | 2.0 | 1.4 V3 | 45.0 |
| 16 | VG 80C | 2.0 | 1.2 V8 | 43.8 |

The test results show that the addition of hydroxyapatite powder according to the invention imparts good flow properties to the various coffee whiteners.

The invention claimed is:

1. A hydroxyapatite powder composed of primary particles, wherein the median size of the primary particles is >0.10 µm and the aspect ratio of the primary particles is <5, wherein the specific surface area of the hydroxyapatite powder is ≤10 m²/g and the bulk density is >550 g/l, wherein the primary particles of the powder are agglomerated to form secondary particles.

2. The hydroxyapatite powder according to claim 1, wherein the hydroxyapatite consists of at least 95 wt % Ca$_5$(PO$_4$)$_3$OH.

3. The hydroxyapatite powder according to claim 1, wherein the hydroxyapatite is calcium-saturated hydroxyapatite with the formula Ca$_5$(PO$_4$)$_3$OH or is calcium-deficient hydroxyapatite with the formula Ca$_{10-x}$(PO$_4$)$_{6-x}$(HPO$_4$)$_x$(OH)$_{2-x}$, wherein 0<x≤2.

4. The hydroxyapatite powder according to claim 1, wherein the median size of the secondary particles is >1.0 µm.

5. A method for producing the hydroxyapatite powder according to claim 1, in which a reaction mixture is created in which milk of lime is reacted with phosphoric acid to form hydroxyapatite, wherein a method cycle comprising the following method steps is carried out:
  a) providing a suspension of hydroxyapatite starter particles in water,
  b) adding milk of lime and phosphoric acid to the suspension,
  c) reacting the milk of lime with the phosphoric acid in the suspension to form hydroxyapatite
    at a temperature in the range of >20° C. and <105° C. and
    at a pH in the range from 6.0 to 13.0,
  d) separating at least a portion of the hydroxyapatite particles out of the suspension,
  e) repeating method steps a) to d) at least once, wherein either the hydroxyapatite particles separated in method step d) or the hydroxyapatite particles remaining in the suspension in method step d) are used as the hydroxyapatite starter particles in method step a), and
  f) removing the hydroxyapatite particles which, in the dried state, have a median size of the primary particles of >0.1 µm from the method cycle.

6. The method according to claim 5, wherein, in said method, the method steps a) to d) are repeated at least 3 times.

7. The method according to claim 5, wherein the method is carried out either
  in semicontinuous operation, wherein the portion of the hydroxyapatite particles separated in method step d), which, in the dried state, has a median size of the primary particles of >0.10 µm, is always removed from the process, while the remaining portion is resuspended in water in method step a) to provide a suspension of hydroxyapatite starter particles in water, or
  in fully continuous operation, wherein, in method step d), the portion of hydroxyapatite particles which, in the dried state, has a median size of the primary particles of >0.10 µm is continuously separated and removed from the method cycle while the remaining portion remains in the method cycle.

8. The method according to claim 5, wherein the milk of lime and the phosphoric acid are added at the same time in step c).

9. The method according to claim 5, wherein the phosphoric acid is diluted phosphoric acid with a concentration of 5-25 vol % of phosphoric acid in water.

10. The method according to claim 5, wherein the oxide-based milk of lime has a concentration of 2-20 wt %.

11. A method comprising adding the hydroxyapatite powder according to claim 1 to foodstuffs to fortify with calcium and/or as a free flowing agent to improve the flow properties of said foodstuffs.

12. A method comprising adding the hydroxyapatite powder according to claim 1 to plastics and ceramics as a filler, to toothpaste as an abrasive, or to brake linings as a hard material.

* * * * *